United States Patent [19]

Hirai et al.

[11] Patent Number: 4,996,286

[45] Date of Patent: * Feb. 26, 1991

[54] TRIHYDRAZIDE LATENT CURING AGENT FOR EPOXY RESINS

[75] Inventors: Kiyomiki Hirai, Kawasaki; Koji Takeuchi, Yokohama; Nobuo Ito, Oiso; Masahiro Abe, Kawasaki, all of Japan

[73] Assignee: Ajinomoto Co., Inc., Tokyo, Japan

[*] Notice: The portion of the term of this patent subsequent to Jul. 23, 2002 has been disclaimed.

[21] Appl. No.: 702,307

[22] Filed: Feb. 15, 1985

[30] Foreign Application Priority Data

Feb. 25, 1984 [JP] Japan ................... 59-34867

[51] Int. Cl.$^5$ .................. C07C 241/04; C08G 59/44
[52] U.S. Cl. .................. 528/123; 528/404.5; 528/365; 528/119; 525/504; 564/151
[58] Field of Search .......... 260/404.5 H PA; 564/151; 528/123, 365, 119, 327; 525/504

[56] References Cited

U.S. PATENT DOCUMENTS

| | | | |
|---|---|---|---|
| 2,847,395 | 8/1958 | Wear | 528/365 X |
| 3,456,006 | 7/1969 | Aelony | 528/123 X |
| 3,467,707 | 9/1969 | Aelony | 260/404.5 |
| 4,530,991 | 7/1985 | Hirai et al. | 528/365 X |
| 4,542,202 | 9/1985 | Takeuchi et al. | 528/365 X |

FOREIGN PATENT DOCUMENTS 105837 10/1974 Japan ................... 260/404.5

OTHER PUBLICATIONS

Ilyashevich et al. CA 83:49043u.

*Primary Examiner*—Carolyn Elmore
*Attorney, Agent, or Firm*—Oblon, Spivak, McClelland, Maier & Neustadt

[57] ABSTRACT

A latent curing agent for epoxy resin, characterized in that the latent curing agent is the hydrazides of the formula (I);

$$(NH_2NHCOCH_2CH_2)_2N(CH_2)_{11}CONHNH_2 \qquad (I)$$

The present curing agent is useful in formulating storable, one-package, heat-curable epoxy resin-based compositions.

5 Claims, No Drawings

TRIHYDRAZIDE LATENT CURING AGENT FOR EPOXY RESINS

BACKGROUND OF THE INVENTION

1. Field of the Invention

The present invention relates to a latent curing agent for epoxy curing resins. More particularly, it relates to a latent curing agent for epoxy resins which causes rapid resin curing at moderate, elevated temperatures and which gives epoxy resin compositions having excellent storage stability at room temperature.

2. Description of the Prior Art

Epoxy resins are widely employed as electric insulating materials, various molded products, adhesives or coatings, because they give valuable cured resins having excellent mechanical, electrical and chemical properties when cured with suitable curing agents for example acid anhydride and amine curing agents. However, epoxy resin composition incorporating amine curing agents cure rapidly at ordinary temperatures and at elevated temperatures and hence they lack storage stability. Also, epoxy resin compositions which incorporate acid anhydride curing agents are stable at ordinary temperatures, but heating for a long period of time at elevated temperature is required for full curing. Usually, tertiary amines, quaternary ammonium compounds or organometal complexes are further added to the composition for purposes of accelerating curing rate. However, the addition of such cure accelerators impairs storage stability markedly.

There have been eagerly desired so-called latent curing agents which are compatible with epoxy resins to form composition which is stable at relatively low temperature and which is rapidly cured when heated to elevated temperature. Representative compounds which have been heretofore proposed as latent curing agents are dicyandiamide, dibasic acid hydrazide, boron trifluorideamine adduct, guanamine, and melamine. Among these compounds, dicyandiamide, dibasic acid hydrazide and guanamine are useful in formulating epoxy resin compositions which have excellent storage stability but full curing by means of these compounds could be achieved by heating at higher temperature than 150° C. for a long time. Also, boron trifluorideamine adduct is hard to treat owing to its highly hygroscopic properties and it affects adversely upon the physical properties of the cured resin.

There has been heretofore known almost no latent epoxy curing agent which causes rapid curing at moderately elevated temperature, that is 100° C.–150° C. and which gives epoxy resin composition having excellent storage stability at ordinary temperature. The epoxy resin compositions which comprise the latent epoxy curing agent are so-called one pack-type epoxy resins.

One-pack type epoxy resins are preferable to the conventional two-pack type epoxy resins because the former cannot be misformulated and can be used continuously. A need therefore continues to exist for an improved curing agent for a one-pack type epoxy resin.

SUMMARY OF THE INVENTION

Accordingly, one object of the present invention is to provide a curing agent for a one-pack epoxy resin composition which effectively cures the resin at low temperatures and which provides for superior storage of the resin.

Briefly, these objects and other objects of the present invention as hereinafter will become more readily apparent can be attained by a curing agent for epoxy resins which is the hydrazide of the formula (I)

$$(NH_2NHCOCH_2CH_2)_2N(CH_2)_{11}CONHNH_2 \qquad (I)$$

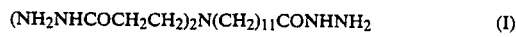

DETAILED DESCRIPTION OF THE PREFERRED EMBODIMENTS

An object of the present invention is to provide novel hydrazide-type curing agent which are useful in making storable one-package curable epoxy resin compositions.

Another object of the present invention is to provide hydrazide-type curing agent which alone or together with other curing agents can activate a rapid curing of epoxy resin composition at relatively low temperature and yet be extraordinarily resistant to gelling at 40° C. for more one month.

Further another object of the present invention is to provide hydrazide-type curing agent which give cured epoxy resin having excellent transparency and flexibility.

The above objects of the present invention may be substantially achieved by providing as curing agent hydrazide compound having the following general formula (I).

$$(NH_2NHCOCH_2CH_2)_2N(CH_2)_{11}CONHNH_2 \qquad (I)$$

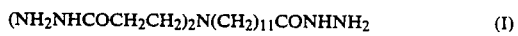

The hydrazide which may be represented by the above general formula (I) is a novel compound which is not disclosed in the literature and may be readily prepared by reacting adduct (A) of 1 mole of the ester of 12-aminododecanoic acid and 2 moles of alkyl acrylate, with hydrazine hydrate, said adduct of amine and dimolecular alkyl acrylate.

$$(R'OC\ O\ CH_2CH_2)_2N(CH_2)_{11}COOR \qquad (A)$$

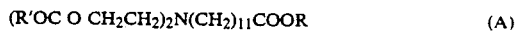

(where R, R' is alkyl group.)

The reacting adduct (A) may be obtained by reacting 1 mole of ester of 12-aminododecanoic acid with 2 moles of alkyl acrylate under present of basic catalysis such as potassium hydroxide in mon- or some kind of solvent such as methanol. Methyl or ethyl acrylate among alkyl acrylates to react with the ester of 12-aminododecanoic acid is very likely available.

The white crystals are obtained by reacting 1 mole of the adduct (A) with three or more moles of hydrazine hydrate in methanol for several hours. After filtration, the crystals were recrystallized from methanol and dried.

The epoxy resin composition incorporating the prescribed amount of the hitherto known dibasic hydrazides, such as adipic acid hydrazide, sebacic acid hydrazide, isophthalic acid hydrazide and the like is cured when heated to 150° C. or higher temperatures. Contrary thereto, the epoxy resin composition incorporating prescribed amount of the hydrazides of the presnt invention has good storage stability and may be cured at 120° C. to 140° C. to give a colorless, transparent and tough cured product.

The required amount of curing agent is determined by the number of active hydrogen atoms in the curing agent employed and the number of epoxy groups in the epoxy resins. In general, 0.5–1.5, preferably 0.7–1.2 equivalents of active hydrogen per equivalent weight of epoxy is employed.

As epoxy resins which may be applied to the hydrazide curing agents of the present invention, various well-known ones having an average of more than 1 epoxy groups in the molecule may be employed. Representative epoxy resins are those based on glycidye ethers of polyhydric phenols, especially the glycidyl ether of Bisphenol A, the glycidyl ether of Bisphenol F and the glycidyl ether of phenolformaldehyde resin.

If necessary, other curing agents, cure accelerator and fillers may be added to the epoxy resin composition of the present invention.

The following examples illustrate the preparation of the hydrazides of the present invention, and usefulness of said hydrazides as latent epoxy curing agent.

Preparation of $(NH_2NHCOCH_2CH_2)_2N(CH_2)_{11}CONHNH_2$ (I): In the flask with the cooling and mixing apparatus, 101.5 g (0.47 mol) of 12-aminododecanoic acid, 600 ml of methanol and 60 g of concentrated hydrochloric acid were mixed. The mixture was heated for 4 hours with stirring. The solution was allowed to stand over night to precipitate the crystals following the concentration at room temperature. After filtration, the crystals were dried in vacuo to obtain 117.3 g (0.44 mol) of methyl 12-amino dodecanolate hydrochloric salt.

39.1 g (0.147 mol) of obtained ester HCl salt was dissolved in methanol. After adding 63.3 g of methyl acrylate and 7.1 g of sodium hydrochloride, the solution was heated for 10 hours at 40° C. After the reaction the reaction solution was concentrated, and 50 ml of ethyl ether and 50 ml of water were added and the mixture was shaken for 10 min, after which the ether and the water layers separated. The ether layer was washed with 30 ml of water twice, anhydrous magunesium sulfate was added to dry the ether layer. Then ether is removed under reduced pressure to obtain 55.2 g (0.138 mol) of light yellowish liquid (A'):

$$(CH_3OCO\ CH_2CH_2)_2N(CH_2)_{11}COOCH_3 \quad (A')$$

Nuclear magnetic resonance (NMR) spectra. δ(ppm) of (A') were showed in below (in chloroform solvent, CDCl TMS standard)

1.28  (18H, $CH_2$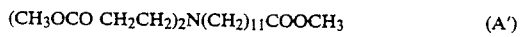$CH_2$)

2.2~2.5 
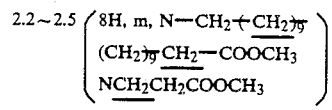

2.74  (4H, t, $NCH_2CH_2COOCH_3$)

3.65  (9H, s, $CH_3OCO—$)

5.52 g of obtained ester (A') was dissolved in 200 ml of methanol, added 34.4 g hydrazine hydrate (80% aqueous solution), stirring for 8 hours at room temperature. By filtration, the white crystals were separated from concentration solution, washed with cold methanol, then recrystallized from methanol, dried in vacuo to obtain 40.5 g (0.101 mol) of prisms.

The analytical values were as shown below.
Melting point: 115°, 117° C.
Elemental analysis:

|  | C | H | N |
|---|---|---|---|
| found (%) | 53.91 | 9.60 | 24.29 |
| calc'd for $C_{12}H_{20}N_6O_2$ (%) | 51.41 | 7.19 | 29.98 |

NMR spectra (in water $D_2O$ DSS standard). δ (ppm)

1.29  (18H, br, $—CH_2(\underline{CH_2})_9CH_2$)

2.1~2.4 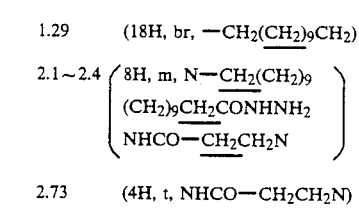

2.73  (4H, t, $NHCO—CH_2\underline{CH_2}N$)

EXAMPLE 2

Reactivity and storage stability of the formulated epoxy resin composition were evaluated.

1. Preparation of the sample

The formulation of the sample is shown in Talbe 1. The individual components were sufficiently mixed in a mortar 2. Evaluation of the reactivity (2-1) Onset temperature and peak temperature were measured by differential thermal analysis (DTA)

| Sample weight | about 10 mg |
|---|---|
| Standard material | $\alpha$-$Al_2O_3$ |
| Heating rate | 5° C./min. |

(2—2) The sample was put into a Geer's oven for 60 minutes and cured temperature was measured.

3. Storage stability

The sample was put into a Geer's oven set to 40° C. and the day required for the sample becoming non-fluidity was measured.

TABLE 1

|  |  | Formulation no. | | | |
|---|---|---|---|---|---|
|  |  | 1 | 2 | 3 | 4 |
| The present invention | Epon 828 *1 | 100 | 100 | 100 | 100 |
|  | Compound | 3 |  |  |  |
|  | Aerosil | 3 |  |  |  |
| Control | Adipic dihydrazide |  | 23 |  |  |
|  | Isophthalic dihydrazide |  |  | 26 |  |
|  | Dicyandizmide |  |  |  | 8 |

*1 A product of Shell Chemical Co. bisphenol A type epoxy resin having epoxy equivalent of 175-120.
*2 A product of Japan Aerosil Co. ultra microsphere silica anhydride

TABLE 2

|  | Formulation No. | Reactivity Onset temp. (°C.) | Reactivity Peak temp. (°C.) | Cure condition (120° C., 60 min) | Storage stability (40° C.) |
|---|---|---|---|---|---|
| The Present invention | No. 1 | 100 | 138 | cured non-colored | 4 weeks |
| Control | No. 2 | 151 | 173 | Not cured | 4 weeks |
|  | No. 3 | 158 | 192 | " | " |
|  | No. 4 | 160 | 199 | " | 4 weeks (Partial separation occured) |

The results in Table 2 show that the latent curing agent for epoxy resin in this invention has excellent storage stability and reactivity. Especially, the reactivity of this agent is superior to the control agent.

What we claim is:

1. A compound of the formula (I):

$$(NH_2NHCOCH_2CH_2)_2N(CH_2)_{11}CONHNH_2 \quad (I)$$

2. A curable epoxy resin composition, comprising:
(a) an epoxy resin having an average of more than one epoxy group per molecule; and
(b) a curing agent of formula (I):

$$(NH_2NHCOCH_2CH_2)_2N(CH_2)_{11}CONHNH_2 \quad (I)$$

3. The curable epoxy resin composition as claimed in claim 2, wherein the amount of said compound is sufficient to provide from 0.5–1.5 active hydrogen equivalents per one equivalent weight of epoxy resin.

4. The curable epoxy resin composition as claimed in claim 2, wherein said epoxy resin is the polyglycidyl ether of a polyhydric phenol.

5. A cured resin obtained by contacting an epoxy resin having an average of more than one epoxy group per molecule with a curing agent having the formula (I):

$$(NH_2NHCOCH_2CH_2)_2N(CH_2)_{11}CONHNH_2 \quad (I)$$

wherein said curing agent is combined with said epoxy resin in an amount sufficient to provide from 0.5–1.5 active hydrogen equivalents per equivalent weight of epoxy resin.

* * * * *